US011911514B2

(12) United States Patent
Lee et al.

(10) Patent No.: US 11,911,514 B2
(45) Date of Patent: Feb. 27, 2024

(54) EXTENDED-RELEASE PHARMACEUTICAL COMPOSITION CONTAINING LACOSAMIDE

(71) Applicant: WHAN IN Pharmaceutical Company, Seoul (KR)

(72) Inventors: Na Kyeom Lee, Anyang-si (KR); Jin Hyeong Park, Suwon-si (KR); Mi Hong Min, Seongnam-si (KR)

(73) Assignee: WHAN IN PHARMACEUTICAL COMPANY, Seoul (KR)

( * ) Notice: Subject to any disclaimer, the term of this patent is extended or adjusted under 35 U.S.C. 154(b) by 324 days.

(21) Appl. No.: 16/969,610

(22) PCT Filed: Jan. 7, 2019

(86) PCT No.: PCT/KR2019/000219
§ 371 (c)(1),
(2) Date: Aug. 13, 2020

(87) PCT Pub. No.: WO2019/160243
PCT Pub. Date: Aug. 22, 2019

(65) Prior Publication Data
US 2021/0023013 A1 Jan. 28, 2021

(30) Foreign Application Priority Data
Feb. 14, 2018 (KR) .................. 10-2018-0018584

(51) Int. Cl.
| *A61K 9/20* | (2006.01) |
| *A61K 9/28* | (2006.01) |
| *A61K 31/165* | (2006.01) |
| *A61K 9/00* | (2006.01) |

(52) U.S. Cl.
CPC ............ *A61K 9/2866* (2013.01); *A61K 9/282* (2013.01); *A61K 31/165* (2013.01); *A61K 9/0053* (2013.01)

(58) Field of Classification Search
None
See application file for complete search history.

(56) References Cited

U.S. PATENT DOCUMENTS

| 2012/0219631 | A1 | 8/2012 | Kulkarni et al. |
| 2013/0017262 | A1* | 1/2013 | Mullen ............... A61K 31/196 514/567 |
| 2013/0251803 | A1* | 9/2013 | Cawello ............... A61K 9/2054 514/616 |
| 2015/0104507 | A1 | 4/2015 | Cawello et al. |
| 2017/0035733 | A1* | 2/2017 | Thoorens ............ A61K 9/0053 |
| 2019/0054009 | A1 | 2/2019 | Cawello et al. |

FOREIGN PATENT DOCUMENTS

| EP | 2 468 261 A1 | 6/2012 |
| EP | 2 878 296 A1 | 6/2015 |
| EP | 3 103 444 A1 | 12/2016 |
| EP | 2 542 227 B1 | 11/2017 |
| KR | 10-2015-0034579 A | 4/2015 |
| KR | 10-1732731 B1 | 5/2017 |
| WO | WO-2011151708 A1 * | 12/2011 ........... A61K 31/195 |

OTHER PUBLICATIONS

International Search Report of PCT/KR2019/000219 dated Apr. 12, 2019 [PCT/ISA/210].
Written Opinion of PCT/KR2019/000219 dated Apr. 12, 2019 [PCT/ISA/237].
Communication dated Oct. 19, 2021 by the European Patent Office in EP Application No. 19 75 4358.
Communication dated May 23, 2023 by the Russian Patent Office in RU Application No. 2020129945 with English translation.

* cited by examiner

*Primary Examiner* — Susan T Tran
(74) *Attorney, Agent, or Firm* — Sughrue Mion, PLLC

(57) ABSTRACT

Disclosed is an extended-release lacosamide preparation which can be taken once a day. Also disclosed is a method for treating a subject with epilepsy including administering the extended-release lacosamide preparation once a day.

7 Claims, 9 Drawing Sheets

[Figure 1]
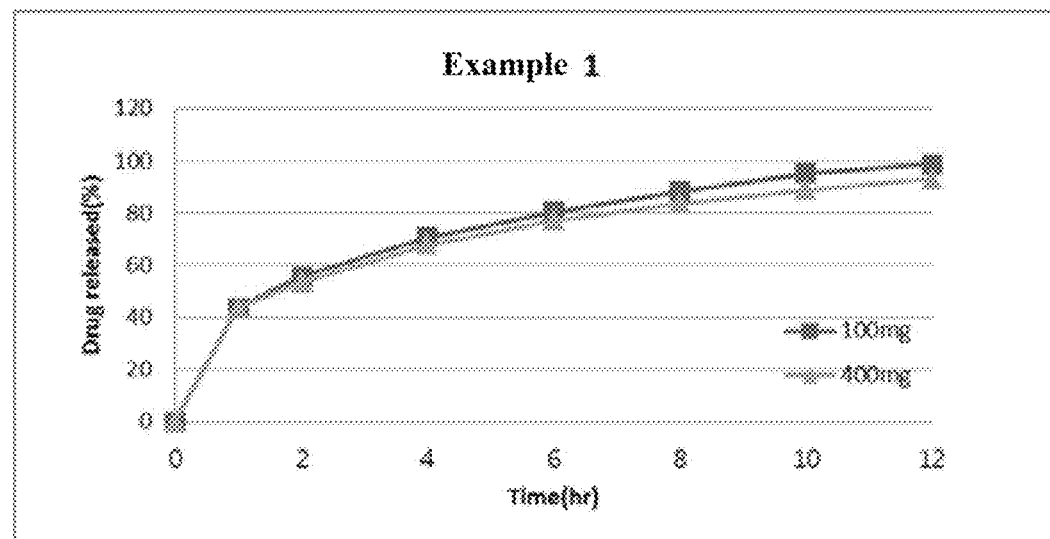
[Figure 2]
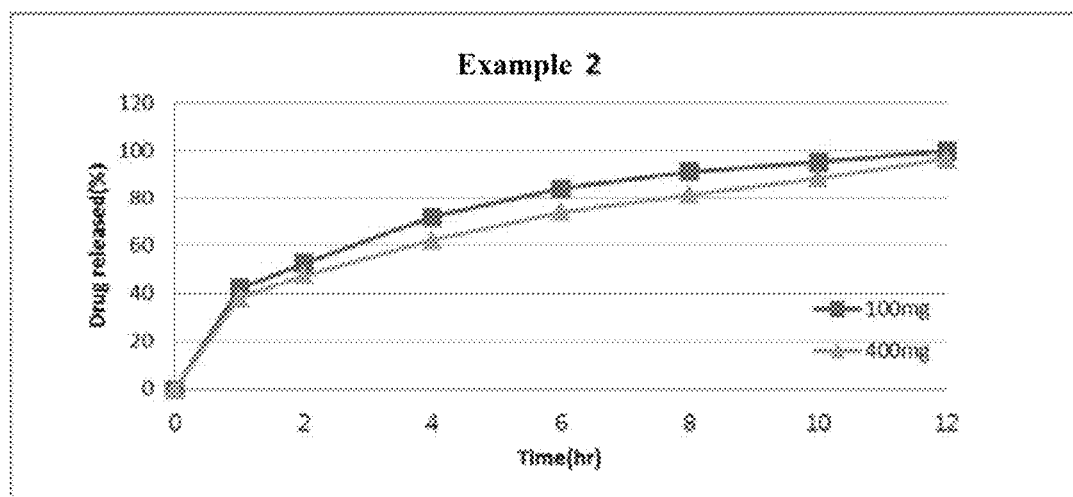

【Figure 3】
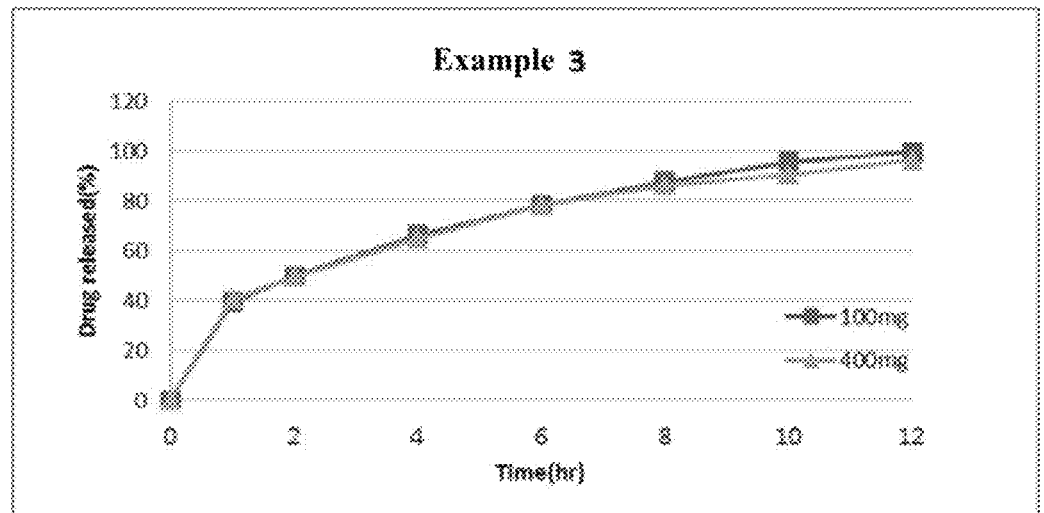
【Figure 4】
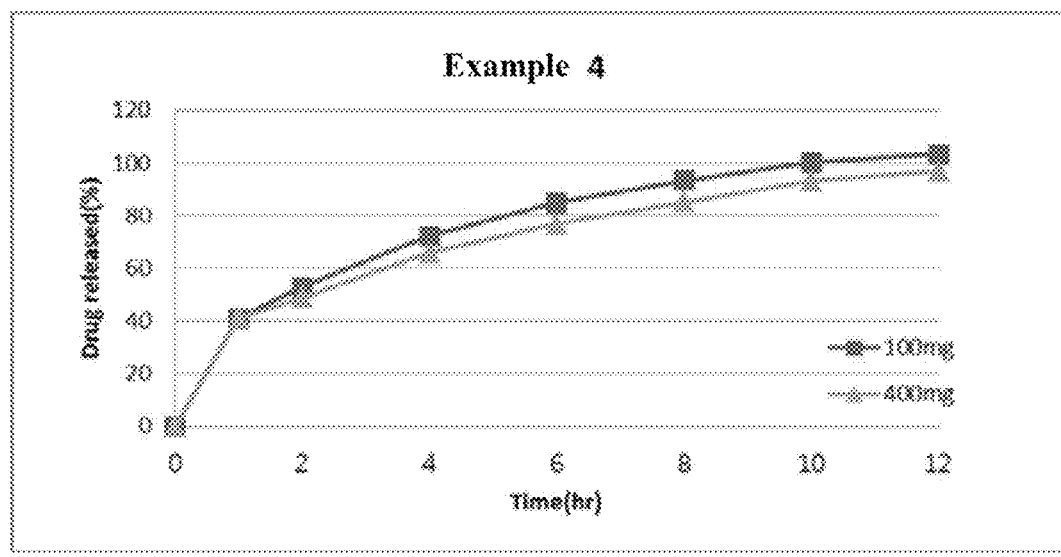

[Figure 5]
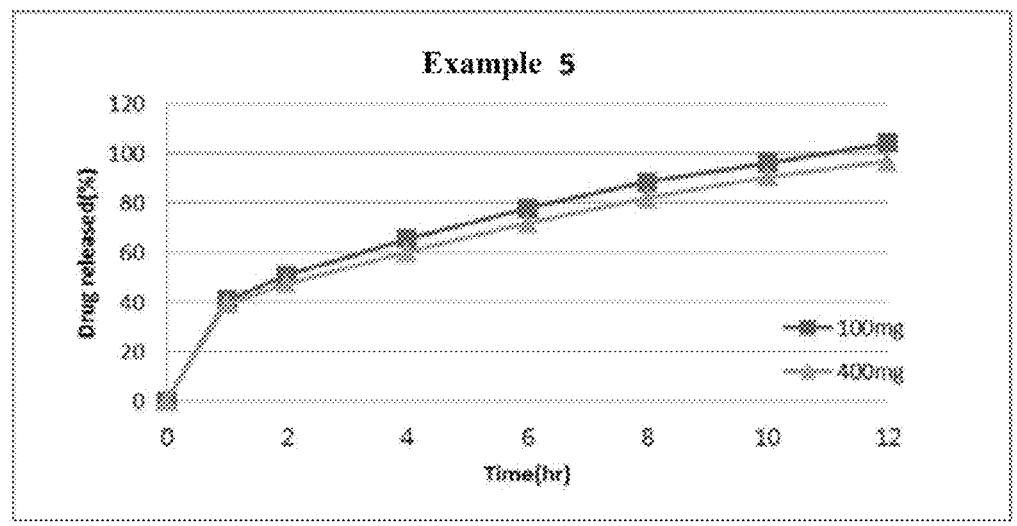
[Figure 6]
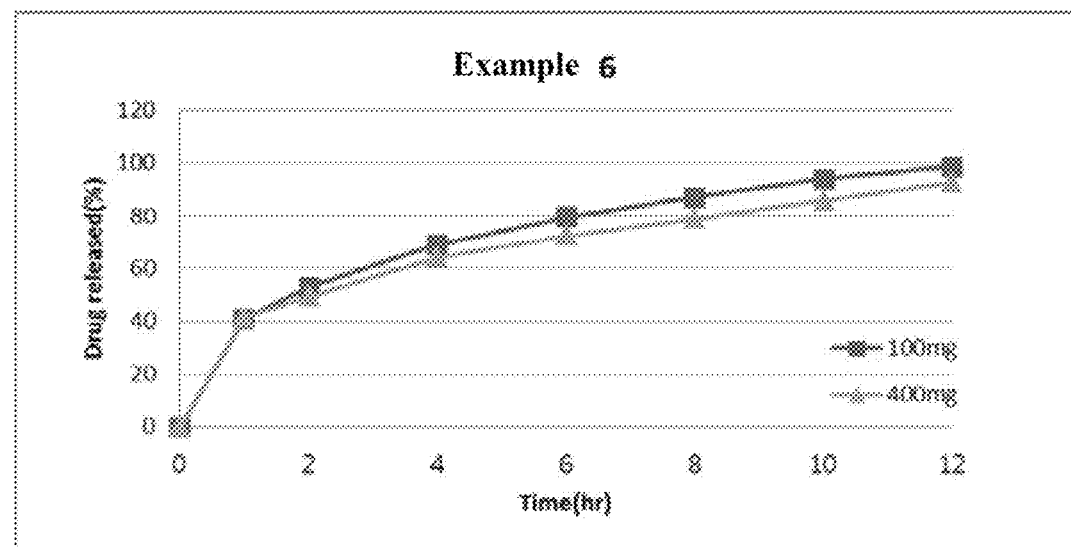

[Figure 7]
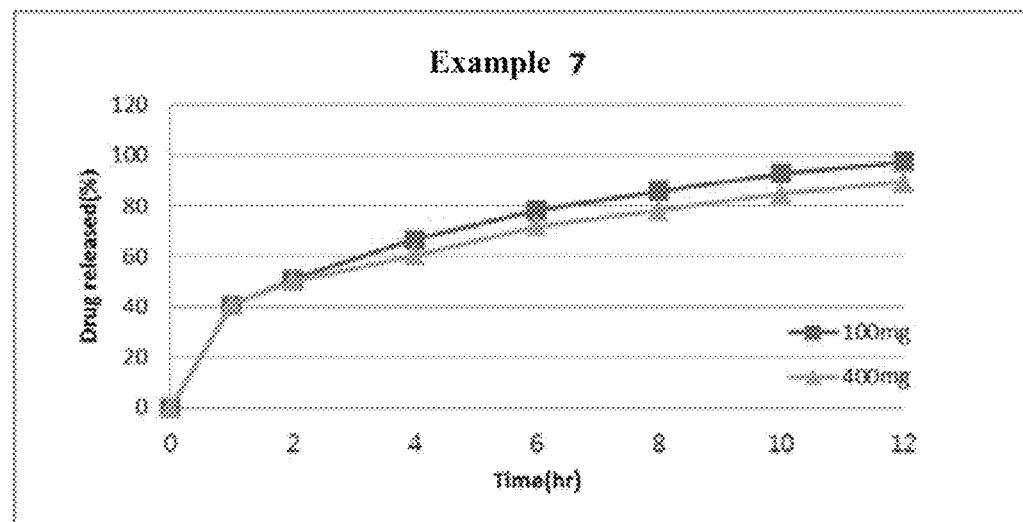
[Figure 8]
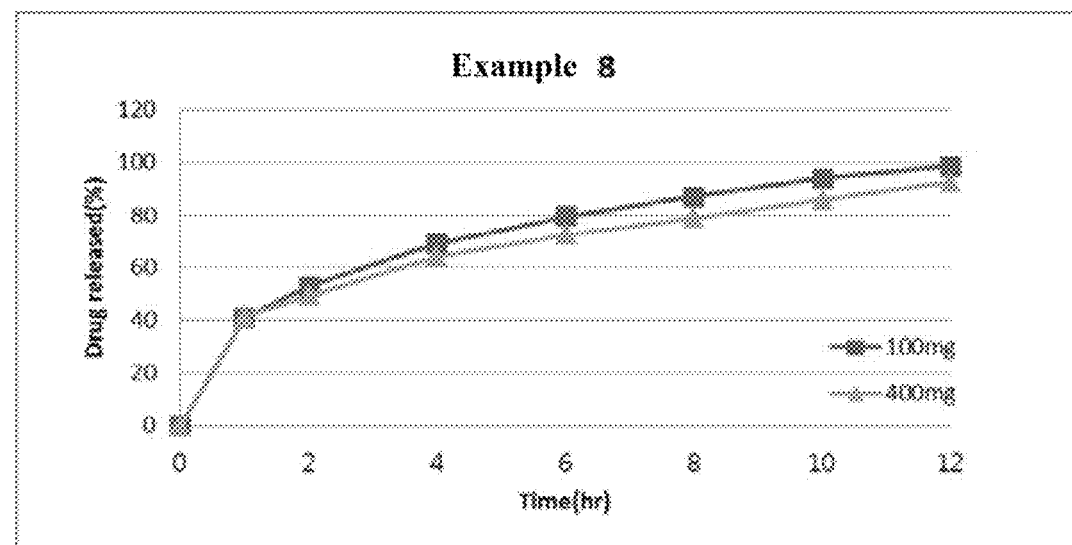

[Figure 9]
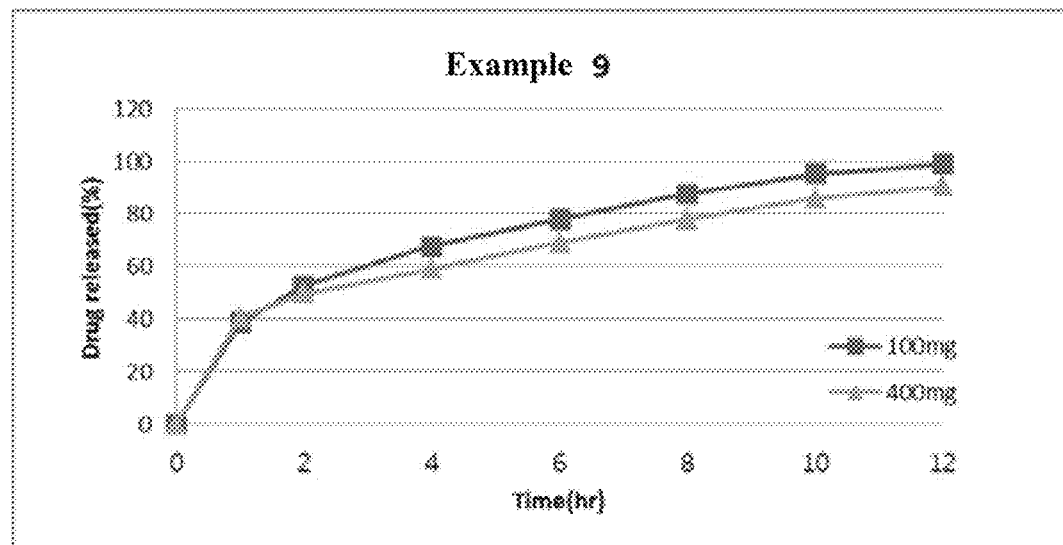
[Figure 10]
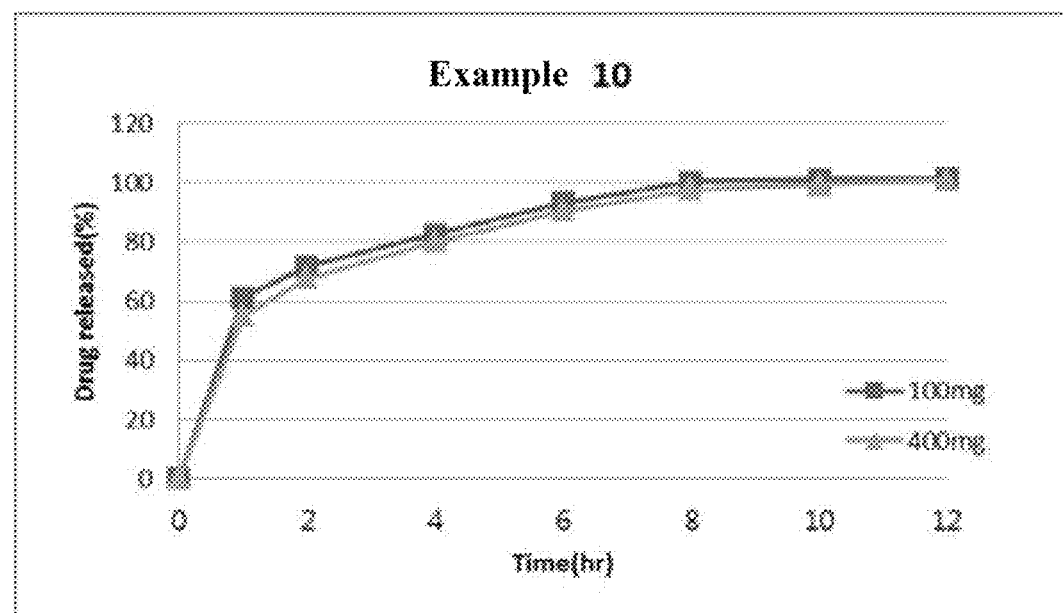

[Figure 11]
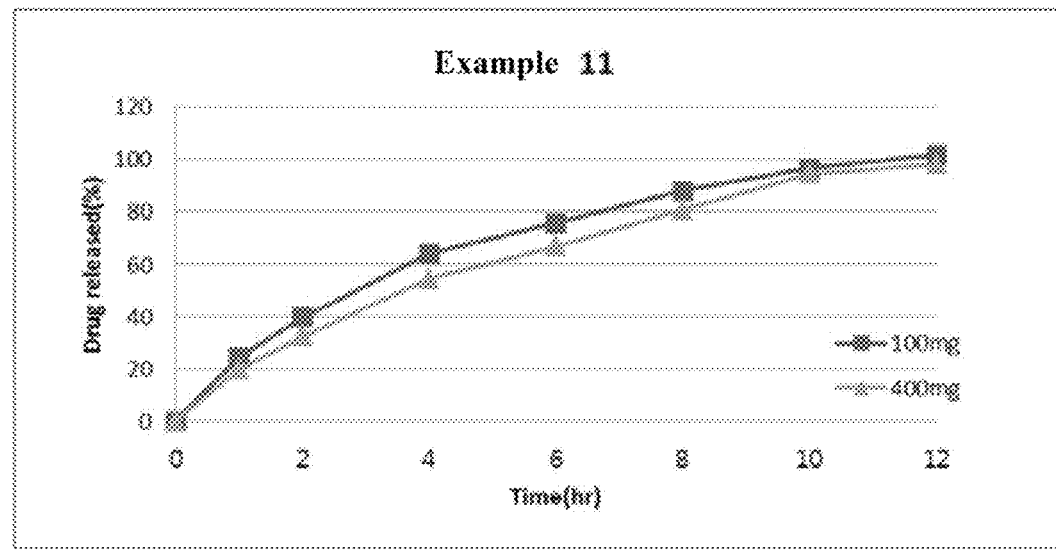
[Figure 12]
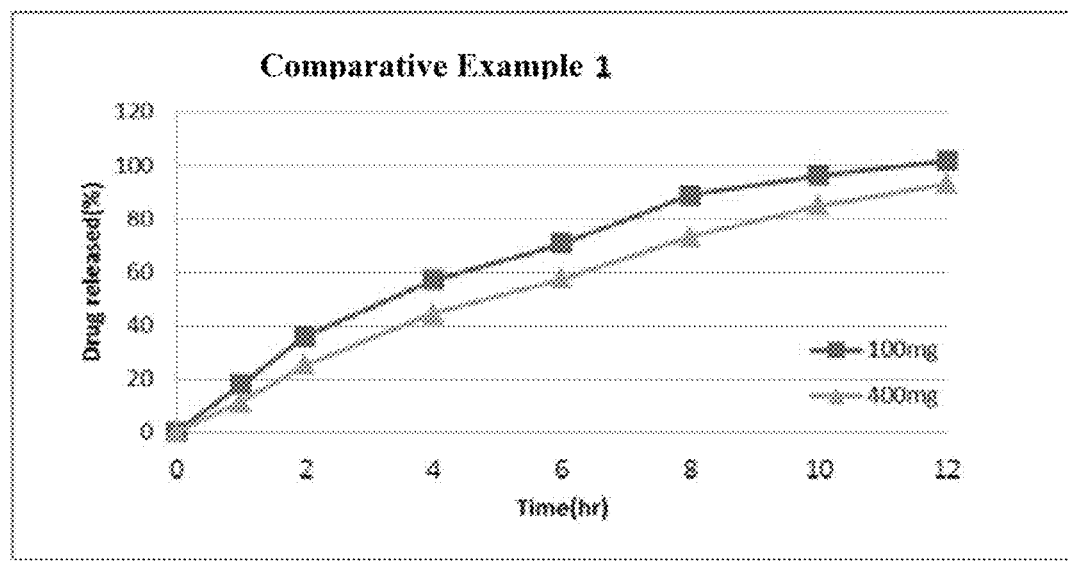

[Figure 13]
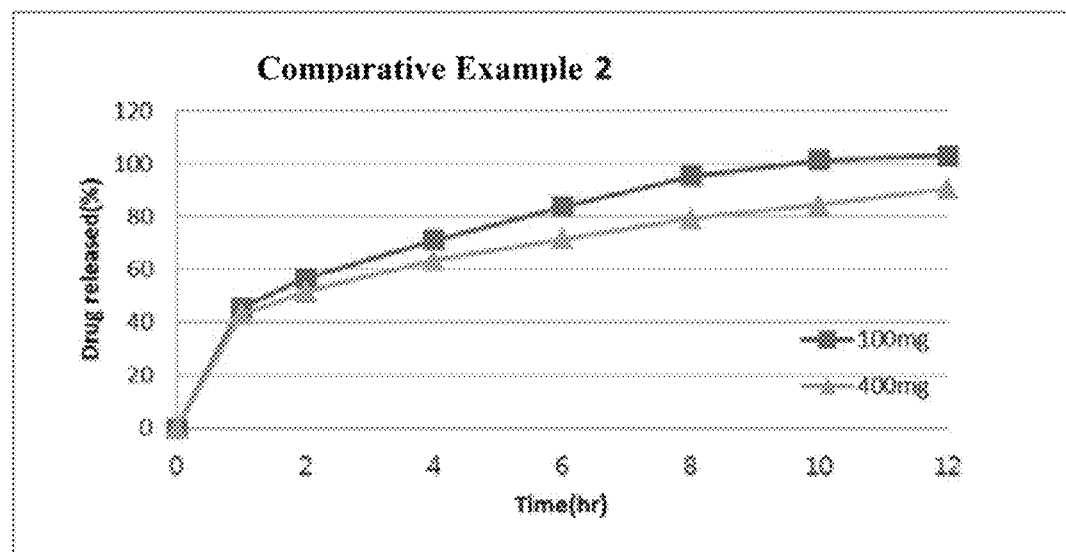
[Figure 14]
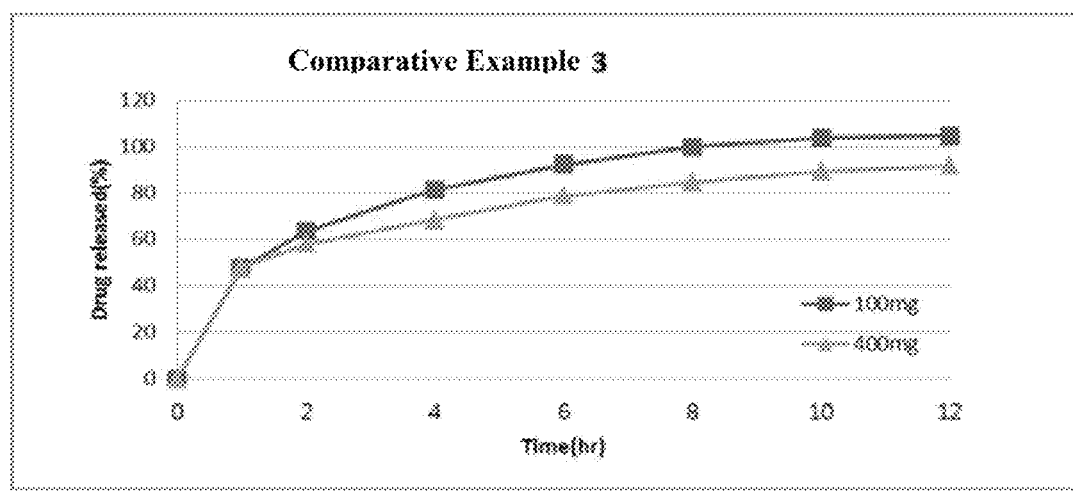

【Figure 15】
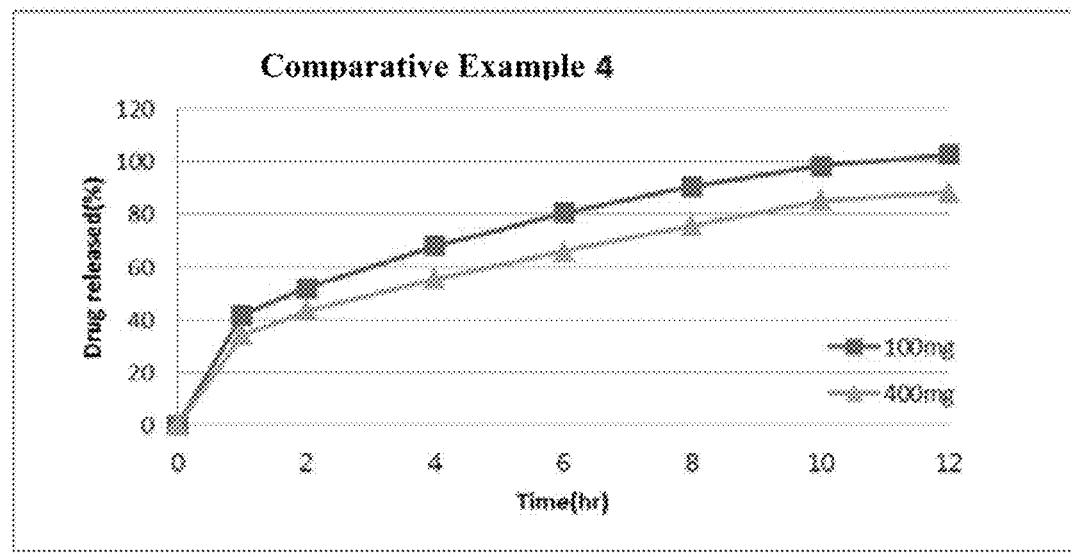
【Figure 16】
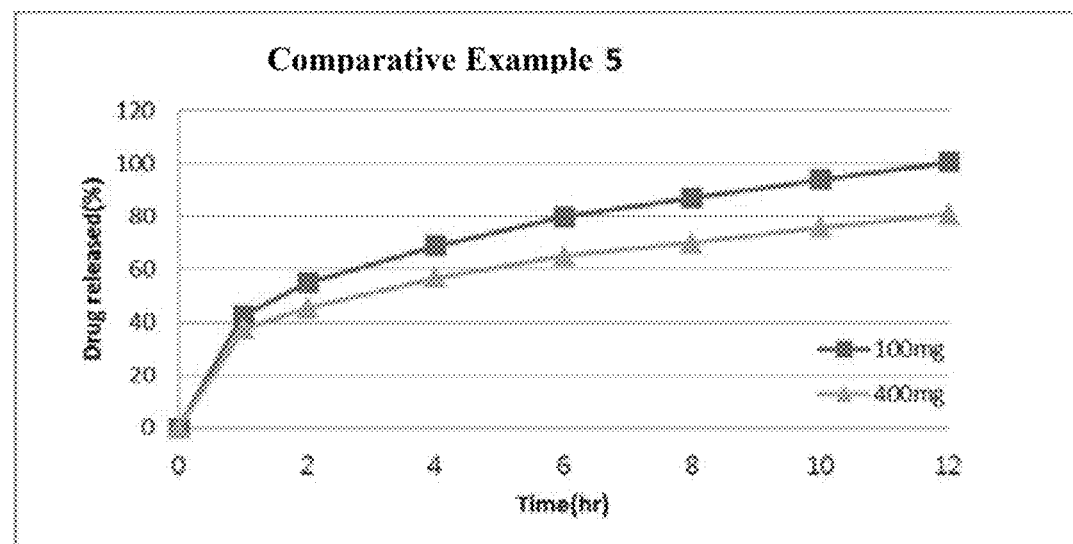

[Figure 17]
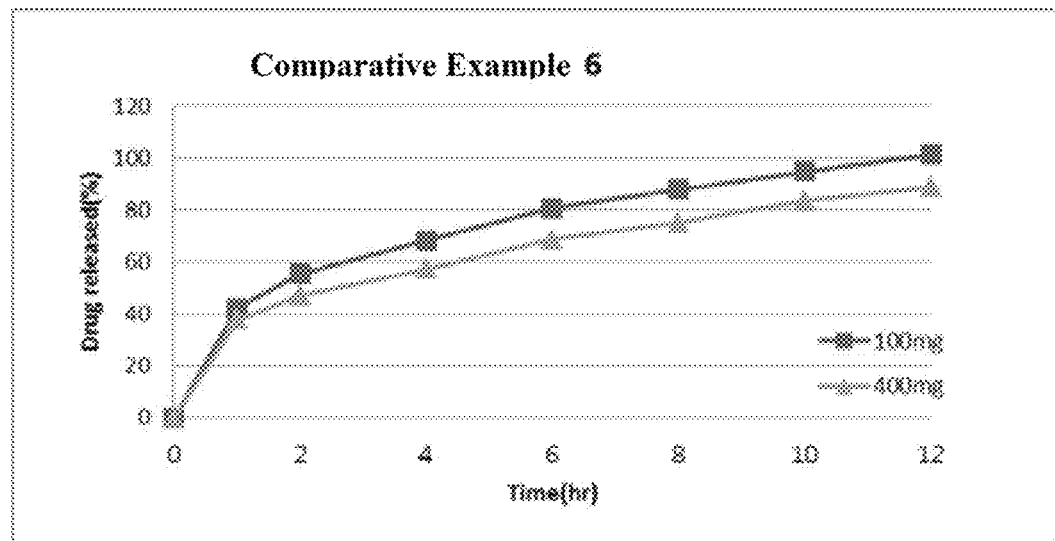
[Figure 18]
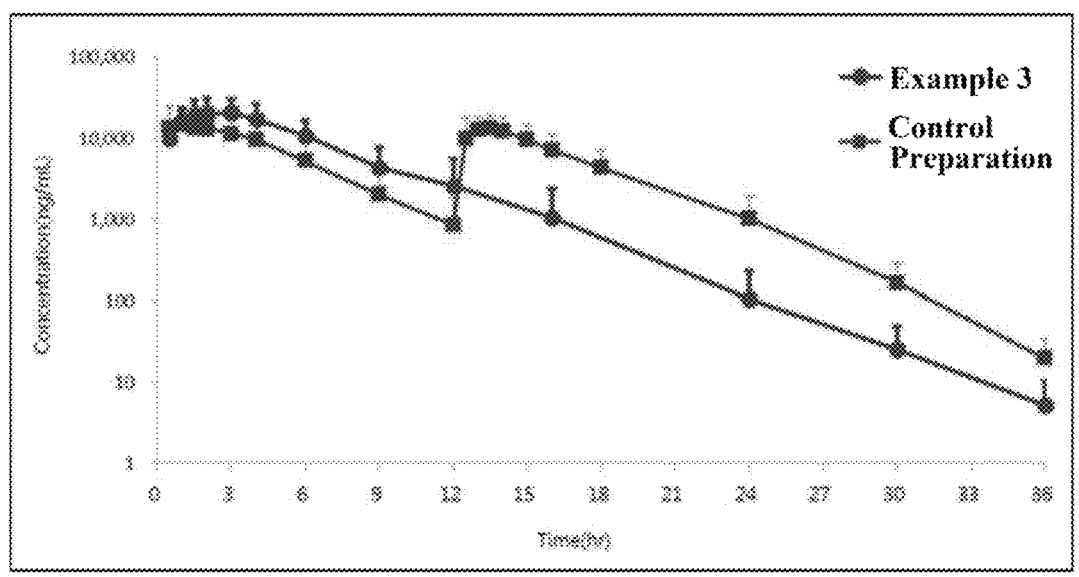

EXTENDED-RELEASE PHARMACEUTICAL COMPOSITION CONTAINING LACOSAMIDE

CROSS REFERENCE TO RELATED APPLICATIONS

This application is a National Stage of International Application No. PCT/KR2019/000219, filed Jan. 7, 2019, claiming priority to Korean Patent Application No. 10-2018-0018584, filed Feb. 14, 2018.

TECHNICAL FIELD

The present invention relates to an extended release pharmaceutical composition containing lacosamide. Specifically, the present invention relates to a lacosamide extended-release preparation that can be taken once a day.

BACKGROUND ART

Epilepsy is estimated to be a disease that affects about 2% of the world's population. In Korea, it is said that epilepsy occurs in about 2.4 people per 1,000 people statistically, and it mainly occurs in older people after their 60s. Epilepsy is caused by disordered electrical phenomena in brain cells. When seizures chronically occur even though there is no specific cause of seizures, it is diagnosed with epilepsy and treatment begins. It is the key to the epilepsy treatment to suppress seizures effectively.

Medicine such as topiramate and zonisamide were used for treatments of epilepsy. Although the mechanism is not clearly revealed, they are reported to act on voltage-gated potassium channels or calcium channels, and excitatory or inhibitory neurotransmitters such as glutamic acid, gamma aminobutyric acid, etc. Lacosamide is a later generation drug disclosed in U.S. Pat. No. 5,773,475, which is reported to have a mechanism to stabilize the hyper-excitatory neuronal membrane by facilitating the slow inactivation of the sodium channel.

Lacosamide has been evaluated as having the best tolerability among epilepsy treatment medicines so far, and it is easy to co-administer since it has less interaction with existing other medicines. Lacosamide is currently used as an adjunct antiepileptic drug to treat partial seizures with or without secondary systemic seizures in patients with epilepsy. Lacosamide is classified as a third-generation antiepileptic drug with a different mechanism of action rather than a first-generation or second-generation antiepileptic drug. In 2010 clinical trials of 1294 patients with epilepsy, it was reported that lacosamide effectively suppress the patient's seizures which could not be controlled by existing other medicine, and also, it was reported that the number of patients with seizures reduced by more than 50% numerically reached 38-49% when taking 400 mg.

Lacosamide's original product name is Vimpat. Vimpat was approved by the US FDA in 2008, and in Korea, it was approved by the Ministry of Food and Drug Safety in 2010 for oral tablets and injections. etc. In Korea, Vimpat is imported by Korea UCB Co. Ltd., and tablets are immediate release type with doses of 50 mg, 100 mg, 150 mg and 200 mg of Lacosamide.

The Vimpat tablet is an immediate-release tablet and should be taken twice a day. Specifically, according to the paragraph of dosage and administration in the medicine guide, the initial recommended dose is 50 mg twice a day, and after a week, the dosage is increased to 100 mg twice a day. Depending on the clinical response and tolerability to this drug, the amount of maintenance dosage can be increased by 50 mg twice a day every week, and the maximum recommended dose is 400 mg per day (200 mg twice a day), unless there is a special disease.

However, epilepsy is a disease that causes chronic seizures even though there are no special factors such as electrolyte imbalance and uremia, etc., and thus, lacosamide is usually required to be taken for a long time. Therefore, reducing the number of administrations per day can bring about a significant improvement in drug compliance. But, there have been no cases in which extended-release tablet of lacosamide which can be taken once a day is developed in Korea. Accordingly, the present inventors tried to develop an extended-release tablet of lacosamide that can be taken once a day.

There are some patent documents that propose an extended release tablet of lacosamide at an idea level.

For example, Korean unexamined Patent Publication No. 10-2015-0034579 says that, when a preparation is implemented as an extended release tablet for once a day by reducing Cmax and delaying Tmax for Cmax in spite of having same AUC as that of an immediate release preparation, the extended release preparation has same clinical efficacy and reduced incidence of adverse effect compared with the immediate-release preparation. Further, it proposed a dissolution profile where about 8.5-41 wt % of lacosamide is released within 1 hour, about 15-64 wt % of lacosamide is released within 2 hours, and about 28-88 wt % of lacosamide is released within 4 hours with respect to the total lacosamide content of the preparation.

In the above patent document, a release profile that can lower Cmax and delay Tmax is specified from simulation by taking into consideration the results of their clinical trials of phase I on the premise that the adverse effect is related to Cmax and that the efficacy is mainly related to AUC. However, since a simulation is just a predictive program, it cannot be confirmed fundamentally that all in the range of dissolution profiles within both the upper and lower limits derived by simulation will satisfy the desired Cmax and AUC for pharmaceutical products, and will exhibit bioequivalence and reduction of adverse effect as is intended. In addition, when the Cmax is low, there is a concern that the initial drug efficacy may not be satisfactory.

Korean Patent gazette No. 10-1732731 points out that the dissolution profiles of extended-release tablets may be different from each other if the content of lacosamide in each tablet is different, and that such problem can be overcome by adjusting the average particle diameter of ethylcellulose polymer particles.

However, since the use of raw materials of ethyl cellulose has a significantly different influence on the dissolution delay effect of tablets depending on the particle size thereof, there is a disadvantage in that it is necessary to precisely control and manage the appropriate particle distribution as well as to secure the average particle size of each excipient in commercialization. In order to commercialize each tablet containing 4 kinds of lacosamide content, there are limitations to continuously secure 4 types of ethylcellulose raw materials having robust particle distribution and to conduct quality control.

DISCLOSURE

Technical Problem

The present inventor tried to develop an extended-release preparation of lacosamide that can be taken once a day. Further, unlike the disclosure of Korean unexamined Patent Publication No. 10-2015-0034579, the present inventor tried to design the preparation's Cmax not to be lower than that of the immediate-release preparation so that there is no lack of initial drug efficacy after taking the drug. Further, unlike the disclosure of Korean Patent gazette No. 10-1732731, the present inventor tried to develop preparations whose dissolution rate profiles show equivalent pattern in each of extended-release tablets having various amounts of lacosamide by using appropriate polymer combinations without adjusting the particle size.

Technical Solution

The present invention has solved the above-mentioned problems with the following means.

1. A pharmaceutical composition comprising lacosamide or a salt thereof as an active ingredient, the composition comprising an immediate release layer and an extended release layer, the extended release layer comprising cellulose derivative and wax or wax-like lipid in a weight ratio of 1:0.1 to 1:10, wherein the pharmaceutical composition can be administered orally once a day.

2. The pharmaceutical composition according to 1 above, wherein the cellulose derivative is at least one selected from the group consisting of hydroxypropyl cellulose, hydroxypropyl methylcellulose, ethylcellulose, methylcellulose and hydroxyethyl cellulose.

3. The pharmaceutical composition according to 1 or 2, wherein the wax or wax-like lipid is at least one selected from the group consisting of glyceryl behenate, glyceryl palmitostearate and glyceryl stearate.

4. The pharmaceutical composition according to any one of 1 to 3, wherein the active ingredient in the immediate release layer and the active ingredient in the extended release layer are in a weight ratio of 1:1 to 1:7.

5. The pharmaceutical composition according to any one of 1 to 4, wherein the content of the cellulose derivative and the wax or wax-like lipid is 5 to 50 wt % with respect to the extended release layer.

Effects

The present invention, even when administered orally once a day, exhibits a bioequivalent to commercially available immediate release preparation which is administered orally twice a day. In addition, the present invention has an advantage that there is no lack of initial drug efficacy compared with simple extended-release tablet since it contains an active ingredient in each of the immediate release layer and the extended release layer, respectively. Furthermore, although it is common that the dissolution rate may be varied depending on the content of the active ingredient since the surface area of the final preparation is varied depending on the content of the active ingredient, the dissolution rate profiles of the present invention are equal to each other even though the content of the active ingredient are different.

DESCRIPTION OF DRAWINGS

FIG. 1 shows the dissolution profiles of 100 mg and 400 mg lacosamide preparation of Example 1.
FIG. 2 shows the dissolution profiles of 100 mg and 400 mg lacosamide preparation of Example 2.
FIG. 3 shows the dissolution profiles of 100 mg and 400 mg lacosamide preparation of Example 3.
FIG. 4 shows the dissolution profiles of 100 mg and 400 mg lacosamide preparation of Example 4.
FIG. 5 shows the dissolution profiles of 100 mg and 400 mg lacosamide preparation of Example 5.
FIG. 6 shows the dissolution profiles of 100 mg and 400 mg lacosamide preparation of Example 6.
FIG. 7 shows the dissolution profiles of 100 mg and 400 mg lacosamide preparation of Example 7.
FIG. 8 shows the dissolution profiles of 100 mg and 400 mg lacosamide preparation of Example 8.
FIG. 9 shows the dissolution profiles of 100 mg and 400 mg lacosamide preparation of Example 9.
FIG. 10 shows the dissolution profile of 100 mg and 400 mg lacosamide preparation of Example 10.
FIG. 11 shows the dissolution profiles of 100 mg and 400 mg lacosamide preparation of Example 11.
FIG. 12 shows the dissolution profiles of 100 mg and 400 mg lacosamide preparation of Comparative Example 1.
FIG. 13 shows the dissolution profiles of 100 mg and 400 mg lacosamide preparation of Comparative Example 2.
FIG. 14 shows the dissolution profiles of 100 mg and 400 mg lacosamide preparation of Comparative Example 3.
FIG. 15 shows the dissolution profiles of 100 mg and 400 mg lacosamide preparation of Comparative Example 4.
FIG. 16 shows the dissolution profiles of 100 mg and 400 mg lacosamide preparation of Comparative Example 5.
FIG. 17 shows the dissolution profiles of 100 mg and 400 mg lacosamide preparation of Comparative Example 6.
FIG. 18 shows the lacosamide blood concentration over time in beagle dogs when lacosamide 200 mg preparation (Example 3) is orally administered once a day and when Vimpat tablet 100 mg (control preparation) is orally administered twice a day.

MODE FOR INVENTION

Lacosamide immediate-release tablets are disclosed. It is Vimpat tablet, and it is taken twice a day. Immediate-release tablets release 98% of the active ingredient within 15 minutes when contact with aqueous medium. Tmax of immediate-release tablets are usually reached within 1.4-1.5 hours after administration, and the excretion half-life is about 13-14 hours. Therefore, immediate-release tablet is ideal for administration of twice a day. Currently, lacosamide is commercially available only as an immediate-release tablet, and no extended-release tablet of lacosamide is commercially available. However, since lacosamide is a drug that requires long-term use due to the nature of the indicated disease for treatment, it has been required to develop a preparation for once a day, the preparation having the same efficacy with that of a preparation for twice a day.

The present invention relates to a lacosamide extended-release tablet that meets the above-mentioned needs.

In the specification, the term "lacosamide" may refer to any component in which the active ingredient is lacosamide. For example, lacosamide or a salt thereof may correspond to this term. Hereinafter, lacosamide or a salt thereof is also referred to as an active ingredient or main ingredient.

The idea of simply extended-release lacosamide exists. However, if the lacosamide formulation is implemented with only an extended-release system, it may be insufficient in the initial drug efficacy compared with that of an immediate-release tablet. Therefore, the present invention is characterized in that it includes both immediate-release and extended-release.

There has been no case in which lacosamide preparation including both immediate-release and extended-release has achieved bioequivalence to the immediate-release tablets which is administered twice a day. However, the present inventor surprisingly found out that, if lacosamide in the immediate-release layer and lacosamide in extended-release layer are in a weight ratio of 1:1 to 1:7 and the extended-release layer comprises cellulose derivative and a wax or wax-like lipid in a weight ratio of 1:0.1 to 1:10 in a preparation, such preparation can be proved to have a bioequivalence.

In addition, although it is generally accepted that dissolution rate profile may be varied since the surface area of the preparation is different depending on the content of the active ingredient, the present inventor found out that if extended-release layer comprises cellulose derivative and a wax or wax-like lipid in a weight ratio of 1:0.1 to 1:10 in a preparation, such preparation has an equivalent dissolution rate profile to each other.

The immediate release layer of the present invention may include active ingredient, disintegrant and filler. If necessary, other additives conventionally used in immediate release tablets may be included.

For example, as the disintegrant, at least one selected from the group consisting of crospovidone, croscarmellose sodium and sodium starch glycolate may be used.

As the filler, at least one selected from the group consisting of microcrystalline cellulose, starch, low-substituted hydroxypropyl cellulose, calcium phosphate and lactose can be used.

The disintegrant and the filler may be appropriately blended with an appropriately ratio by a skilled person in the art considering the content of the active ingredient. For example, they may be added in the amount of 10 to 80 wt %, preferably 10 to 50 wt % based on the immediate release layer, respectively.

The immediate release layer of the present invention may further comprise glidant, binder, lubricant, and the like, if necessary. For example, as the glidant, at least one selected from the group consisting of calcium silicate, colloidal silicon dioxide, magnesium aluminometasilicate and talc may be used. As the binder, at least one selected from the group consisting of povidone, hydroxypropyl cellulose and copovidone may be used. As the lubricant, at least one selected from the group consisting of sodium stearyl fumarate, stearic acid and magnesium stearate may be used. The blending ratio may also be appropriately adjusted by a person skilled in the art. For example, they may be included in the amount of 1 to 30 wt %, preferably 1 to 10 wt % based on the immediate release layer, respectively.

The immediate release layer of the present invention may be prepared by mixing lacosamide, glidant, and filler, adding binder, granulating, sizing the granulation and then mixing with disintegrant and lubricant.

The extended release layer of the present invention includes active ingredient and base for controlled-release. The base for controlled-release is characterized in that the cellulose derivative and the wax or wax-like lipid are blended in a weight ratio of 1:0.1 to 1:10. The base for controlled-release may be included in the amount of 5 to 50 wt %, preferably 5 to 40 wt %. If the content of the base for control-release exceeds 50 wt %, the drug is too slowly released, and thus, the controlled release cannot be achieved and the size of the tablet increases, which causes decrease of drug compliance. If the content of the base for control-release is less than 5 wt %, the release of the drug becomes faster, and thus, the continuous controlled-release cannot be achieved.

The extended-release layer of the present invention may further be suitably blended with the above-mentioned glidant, filler, binder, and lubricant. For example, as the filler, at least one selected from the group consisting of microcrystalline cellulose, starch, low-substituted hydroxypropyl cellulose, calcium phosphate and lactose may be used. As glidant, at least one selected from the group consisting of calcium silicate, colloidal silicon dioxide, magnesium aluminometasilicate and talc may be used. As binder, at least one selected from the group consisting of povidone, hydroxypropyl cellulose and copovidone may be used. As lubricant, at least one selected from the group consisting of sodium stearyl fumarate, stearic acid and magnesium stearate may be used. For example, they may be included in the amount of 1 to 50 wt %, preferably 1 to 30 wt % based on the extended release layer, respectively.

The extended-release layer of the present invention may be prepared by mixing lacosamide, glidant, filler and base for controlled-release, adding binder, granulating, sizing the granulation and then mixing lubricant.

The final preparation can be obtained as two-layered tablets by tableting the immediate-release layer and the extended-release layer. If necessary, the obtained tablets may be coated. As the film coating base, at least one selected from the group consisting of hydroxypropyl methyl cellulose and polyvinyl alcohol may be used. The film coating base may be 1-10 wt % based on tablet.

The present invention can be a preparation containing 100 mg, 200 mg, 300 mg, 400 mg content on the basis of lacosamide.

EXAMPLES

Hereinafter, the present invention will be more detailed illustrated with following examples. However, it should be noted that following examples are only embodiments of the present invention, and the scope of the present invention is not limited thereby.

1. Examples 1-1. Extended-Release Base Ingredient (Active Ingredient 200 mg Prescription Table)

TABLE 1

| | Ingredient | Example 1 | Example 2 | Example 3 |
|---|---|---|---|---|
| Extended release | Lacosamide | 150.0 | 150.0 | 150.0 |
| | Colloidal silicon dioxide | 9.0 | 9.0 | 9.0 |
| | Microcrystalline cellulose | 78.0 | 78.0 | 78.0 |
| | Hydroxypropyl cellulose | 10.0 | 10.0 | 10.0 |
| | Ethyl cellulose | 20.0 | — | — |
| | Hydroxy propyl methyl cellulose | — | 20.0 | — |
| | Hydroxyethyl cellulose | — | — | 20.0 |
| | Glyceryl behenate | 20.0 | 20.0 | 20.0 |
| | Magnesium stearate | 3.0 | 3.0 | 3.0 |
| Immediate release | Lacosamide | 50.0 | 50.0 | 50.0 |
| | Colloidal silicon dioxide | 4.0 | 4.0 | 4.0 |
| | Low-substituted hydroxypropyl cellulose | 22.0 | 22.0 | 22.0 |
| | Microcrystalline cellulose | 60.5 | 60.5 | 60.5 |
| | Hydroxypropyl cellulose | 5.0 | 5.0 | 5.0 |
| | Crospovidone | 7.0 | 7.0 | 7.0 |
| | Magnesium stearate | 1.5 | 1.5 | 1.5 |
| | coating | 13.2 | 13.2 | 13.2 |
| | Total (mg/tablet) | 453.2 | 453.2 | 453.2 |

* Unit: mg (same in following tables)

The extended release layer is prepared by mixing lacosamide with colloidal silicon dioxide, microcrystalline cellulose, extended-release polymer (base for controlled-release) and wax or wax-like lipids, and then adding binder wherein hydroxypropyl cellulose is dissolved, kneading, granulating, drying at a temperature of 60° C. for 1-2 hours in a dryer, sizing the granulation and mixing with lubricant.

The immediate release layer is prepared by mixing lacosamide with colloidal silicon dioxide, microcrystalline cellulose and low-substituted hydroxypropyl cellulose, and then adding binder wherein hydroxypropyl cellulose is dissolved, kneading, granulating, drying at a temperature of 60° C. for 1-2 hours in a dryer, sizing the granulation and mixing with disintergrant and lubricant.

The extended-release granules and the immediate-release granules prepared in the above are compressed into two-layered tablets, and the obtained tablets are coated with hydroxypropyl methyl cellulose or polyvinyl alcohol based Opadry coating agent according to a conventional method to obtain extended-release tablets comprising lacosamide 200 mg per film coated tablet.

Extended-release tablets of lacosamide 100 mg, 200 mg, 300 mg and 400 mg are prepared according to a multiplied prescription wherein the amount of each component in the based prescription is multiplied by a factor, respectively.

1-2. Content Ratio of Extended-Release Base Combination

TABLE 2

|  | Ingredient | Example 4 | Example 5 | Example 6 | Example 7 | Example 8 | Example 9 |
|---|---|---|---|---|---|---|---|
| Extended release | Lacosamide | 150.0 | 150.0 | 150.0 | 150.0 | 150.0 | 150.0 |
|  | Colloidal silicon dioxide | 9.0 | 9.0 | 9.0 | 9.0 | 9.0 | 9.0 |
|  | Microcrystalline cellulose | 78.0 | 78.0 | 78.0 | 78.0 | 78.0 | 78.0 |
|  | Hydroxypropyl cellulose | 10.0 | 10.0 | 10.0 | 10.0 | 10.0 | 10.0 |
|  | Hydroxyethyl cellulose | 36.0 | 25.0 | 15.0 | 10.0 | 5.0 | 3.6 |
|  | Glyceryl behenate | 4.0 | 15.0 | 25.0 | 30.0 | 35.0 | 36.4 |
|  | Magnesium stearate | 3.0 | 3.0 | 3.0 | 3.0 | 3.0 | 3.0 |
| Immediate release | Lacosamide | 50.0 | 50.0 | 50.0 | 50.0 | 50.0 | 50.0 |
|  | Colloidal silicon dioxide | 4.0 | 4.0 | 4.0 | 4.0 | 4.0 | 4.0 |
|  | Low-substituted hydroxypropyl cellulose | 22.0 | 22.0 | 22.0 | 22.0 | 22.0 | 22.0 |
|  | Microcrystalline cellulose | 60.5 | 60.5 | 60.5 | 60.5 | 60.5 | 60.5 |
|  | Hydroxypropyl cellulose | 5.0 | 5.0 | 5.0 | 5.0 | 5.0 | 5.0 |
|  | Crospovidone | 7.0 | 7.0 | 7.0 | 7.0 | 7.0 | 7.0 |
|  | Magnesium stearate | 1.5 | 1.5 | 1.5 | 1.5 | 1.5 | 1.5 |
|  | coating | 13.2 | 13.2 | 13.2 | 13.2 | 13.2 | 13.2 |
|  | Total (mg/tablet) | 453.2 | 453.2 | 453.2 | 453.2 | 453.2 | 453.2 |

Lacosamide extended-release tablets having various ratio of hydroxyethyl cellulose (HEC)/glyceryl behenate (GB) (1:0.1 to 1:10) were prepared according to the same manufacturing method as in Example 1-1.

1-3. Active Ingredient Content Ratio

TABLE 3

|  | Ingredient | Example 10 | Example 11 | Comparative Example 1 |
|---|---|---|---|---|
| Extended release | Lacosamide | 100.0 | 175.0 | 200.0 |
|  | Colloidal silicon dioxide | 9.0 | 9.0 | 9.0 |
|  | Microcrystalline cellulose | 141.4 | 46.4 | 14.6 |
|  | Hydroxypropyl cellulose | 10.0 | 10.0 | 10.0 |
|  | Hydroxyethyl cellulose | 13.3 | 23.3 | 26.7 |
|  | Glyceryl behenate | 13.3 | 23.3 | 26.7 |
|  | Magnesium stearate | 3.0 | 3.0 | 3.0 |
| Immediate release | Lacosamide | 100.0 | 25.0 | — |
|  | Colloidal silicon dioxide | 4.0 | 4.0 | 4.0 |
|  | Low-substituted hydroxypropyl cellulose | 22.0 | 22.0 | 22.0 |
|  | Microcrystalline cellulose | 10.5 | 85.5 | 110.5 |
|  | Hydroxypropyl cellulose | 5.0 | 5.0 | 5.0 |
|  | Crospovidone | 7.0 | 7.0 | 7.0 |
|  | Magnesium stearate | 1.5 | 1.5 | 1.5 |
|  | coating | 13.2 | 13.2 | 13.2 |
|  | Total (mg/tablet) | 453.2 | 453.2 | 453.2 |

Lacosamide extended-release tablets having various amount of active ingredient were prepared according to the same manufacturing method as in Example 1.1.

2. Comparative Examples 2-1. Ingredient of Base for Extended-Release

TABLE 4

|  | Ingredient | Comparative Example 2 | Comparative Example 3 | Comparative Example 4 | Comparative Example 5 |
|---|---|---|---|---|---|
| Extended release | Lacosamide | 150.0 | 150.0 | 150.0 | 150.0 |
|  | Colloidal silicon dioxide | 9.0 | 9.0 | 9.0 | 9.0 |
|  | Microcrystalline cellulose | 78.0 | 78.0 | 78.0 | 78.0 |
|  | Hydroxypropyl cellulose | 10.0 | 10.0 | 10.0 | 10.0 |
|  | Ethyl cellulose | 40.0 |  |  |  |
|  | Hydroxypropyl methyl cellulose |  | 40.0 |  |  |
|  | Hydroxyethyl cellulose |  |  | 40.0 |  |
|  | Glyceryl behenate |  |  |  | 40.0 |
|  | Magnesium stearate | 3.0 | 3.0 | 3.0 | 3.0 |
| Immediate release | Lacosamide | 50.0 | 50.0 | 50.0 | 50.0 |
|  | Colloidal silicon dioxide | 4.0 | 4.0 | 4.0 | 4.0 |
|  | Low-substituted hydroxypropyl cellulose | 22.0 | 22.0 | 22.0 | 22.0 |
|  | Microcrystalline cellulose | 60.5 | 60.5 | 60.5 | 60.5 |
|  | Hydroxy propyl cellulose | 5.0 | 5.0 | 5.0 | 5.0 |
|  | Crospovidone | 7.0 | 7.0 | 7.0 | 7.0 |

TABLE 4-continued

| Ingredient | | Comparative Example 2 | Comparative Example 3 | Comparative Example 4 | Comparative Example 5 |
|---|---|---|---|---|---|
| Magnesium stearate | | 1.5 | 1.5 | 1.5 | 1.5 |
| coating | | 13.2 | 13.2 | 13.2 | 13.2 |
| Total (mg/tablet) | | 453.2 | 453.2 | 453.2 | 453.2 |

Lacosamide extended-release tablets having various extended-release polymer were prepared according to the same manufacturing method as in Example 1-1.

2-2. Content Ratio of Extended-Release Base Combination

TABLE 5

| | | Comparative Example 6 |
|---|---|---|
| Extended release | Lacosamide | 150.0 |
| | Colloidal silicon dioxide | 9.0 |
| | Microcrystalline cellulose | 78.0 |
| | Hydroxypropyl cellulose | 10.0 |
| | Hydroxyethyl cellulose | 3.3 |
| | Glyceryl behenate | 36.7 |
| | Magnesium stearate | 3.0 |
| Immediate release | Lacosamide | 50.0 |
| | Colloidal silicon dioxide | 4.0 |
| | Low-substituted hydroxypropyl cellulose | 22.0 |
| | Microcrystalline cellulose | 60.5 |
| | Hydroxypropyl cellulose | 5.0 |
| | Crospovidone | 7.0 |
| | Magnesium stearate | 1.5 |
| | coating | 13.2 |
| Total (mg/tablet) | | 453.2 |

Lacosamide extended-release tablets having various ratio of hydroxyethyl cellulose/glyceryl behenate were prepared according to the same manufacturing method as in Example 1-1.

3. Experimental Example 3-1. Dissolution Rate Evaluation (Examples 1-3)

Dissolution rate of each preparation of Examples 1 to 3 were evaluated according to the second method (paddle method) of the Korean Pharmacopoeia Dissolution Test Method using the condition of 900 ml purified water at 50 rpm. The dissolution test solution was analyzed by HPLC after 0.45 um filter of PVDF. Analysis conditions were as follows.

<Analysis Condition>

Column: a column of stainless steel pipe having an inside diameter of about 4.6 mm and a length of about 50 mm filled with 3 μm octadecylsilyl silica gel for liquid chromatography (Ultracarb ODS, 4.6×50 mm, 3 μm) or its equivalent column Mobile phase: water•acetonitrile•trifluoroacetic acid (v/v/v)=700•300•1

Detection wavelength: UV, 215 nm

Injection volume: 2 uL

Flow rate: 1.0 mL/min

Dissolution profiles of 100 mg and 400 mg preparation prepared according to Examples 1 to 3 were evaluated and the results are shown in Table 6.

TABLE 6

| | Example 1 | | Example 2 | | Example 3 | |
|---|---|---|---|---|---|---|
| Hour(hr) | 100 mg | 400 mg | 100 mg | 400 mg | 100 mg | 400 mg |
| 1 | 43.7 | 43.5 | 42.0 | 38.1 | 39.4 | 40.5 |
| 2 | 55.6 | 53.3 | 52.7 | 47.5 | 49.8 | 49.4 |
| 4 | 70.8 | 68.1 | 71.9 | 62.1 | 66.2 | 64.9 |
| 6 | 80.4 | 77.3 | 83.9 | 74.0 | 78.1 | 78.1 |
| 8 | 88.1 | 83.2 | 91.3 | 91.5 | 87.8 | 86.2 |
| 10 | 95.3 | 88.9 | 95.2 | 88.5 | 95.7 | 90.5 |
| 12 | 98.9 | 93.3 | 99.8 | 96.6 | 99.5 | 96.4 |

3-2. Dissolution Rate Evaluation (Examples 4 to 9)

Dissolution profiles of 100 mg and 400 mg preparations prepared according to Examples 4 to 9 were evaluated according to the same method as in the Experiment Example 3-1 of dissolution rate evaluation. The results are shown in Tables 7-8 below.

TABLE 7

| | Example 4 | | Example 5 | | Example 6 | |
|---|---|---|---|---|---|---|
| Hour(hr) | 100 mg | 400 mg | 100 mg | 400 mg | 100 mg | 400 mg |
| 1 | 40.7 | 41.1 | 40.5 | 39.1 | 43.0 | 39.2 |
| 2 | 53.0 | 48.9 | 51.1 | 47.5 | 53.9 | 49.7 |
| 4 | 72.4 | 65.8 | 65.8 | 60.3 | 67.3 | 61.5 |
| 6 | 84.9 | 77.1 | 77.9 | 71.9 | 77.8 | 73.3 |
| 8 | 93.5 | 85.1 | 88.7 | 82.0 | 88.0 | 83.8 |
| 10 | 100.3 | 93.3 | 96.2 | 90.8 | 95.4 | 89.6 |
| 12 | 103.5 | 97.0 | 104.0 | 97.0 | 100.4 | 96.8 |

TABLE 8

| | Example 7 | | Example 8 | | Example 9 | |
|---|---|---|---|---|---|---|
| Hour(hr) | 100 mg | 400 mg | 100 mg | 400 mg | 100 mg | 400 mg |
| 1 | 40.9 | 41.3 | 40.7 | 41.2 | 38.6 | 40.7 |
| 2 | 51.1 | 50.3 | 52.9 | 49.3 | 52.7 | 49.6 |
| 4 | 66.8 | 60.5 | 69.2 | 64.2 | 67.7 | 60.9 |
| 6 | 78.5 | 72.1 | 79.6 | 72.5 | 77.8 | 68.9 |
| 8 | 86.0 | 78.3 | 87.2 | 79.0 | 87.6 | 77.8 |
| 10 | 93.0 | 84.9 | 94.2 | 85.9 | 95.1 | 85.7 |
| 12 | 97.6 | 89.5 | 98.9 | 92.8 | 99.0 | 90.6 |

3-3. Dissolution Rate Evaluation (Examples 10-11, Comparative Example 1)

Dissolution profile of the 400 mg preparations prepared according to Examples 10 to 11 was evaluated according to the same method as in the Experiment Example 3-1 of dissolution rate evaluation. The results are shown in Table 9 below.

TABLE 9

|  | Example 10 | | Example 11 | | Comparative Example 1 | |
|---|---|---|---|---|---|---|
| Hour(hr) | 100 mg | 400 mg | 100 mg | 400 mg | 100 mg | 400 mg |
| 1 | 61.2 | 55.1 | 24.5 | 20.1 | 18.1 | 11.4 |
| 2 | 71.6 | 67.7 | 39.7 | 32.5 | 36.0 | 25.2 |
| 4 | 82.5 | 80.0 | 63.9 | 54.5 | 57.0 | 44.5 |
| 6 | 93.2 | 90.4 | 75.8 | 67.0 | 70.6 | 57.4 |
| 8 | 100.1 | 97.7 | 87.9 | 80.7 | 88.8 | 73.1 |
| 10 | 101.2 | 99.4 | 96.6 | 94.5 | 96.4 | 85.1 |
| 12 | 101.4 | 100.8 | 101.5 | 98.1 | 101.7 | 93.2 |

3-4. Dissolution Rate Evaluation (Comparative Examples 2 to 6)

Dissolution profiles of 100 mg and 400 mg preparations prepared according to Comparative Examples 2 to 6 were evaluated according to the same method as in the Experiment Example 3-1 of dissolution rate evaluation. The results are shown in Tables 10-11 below.

TABLE 10

|  | Comparative Example 2 | | Comparative Example 3 | | Comparative Example 4 | |
|---|---|---|---|---|---|---|
| Hour(hr) | 100 mg | 400 mg | 100 mg | 400 mg | 100 mg | 400 mg |
| 1 | 45.4 | 42.9 | 47.8 | 48.1 | 41.8 | 34.1 |
| 2 | 56.5 | 51.5 | 63.5 | 58.0 | 51.8 | 43.4 |
| 4 | 71.1 | 63.6 | 81.4 | 68.5 | 67.9 | 55.5 |
| 6 | 83.8 | 71.7 | 92.4 | 79.0 | 80.5 | 65.8 |
| 8 | 95.3 | 79.2 | 100.1 | 85.1 | 90.5 | 75.7 |
| 10 | 101.3 | 84.4 | 103.8 | 89.7 | 98.3 | 85.2 |
| 12 | 103.1 | 90.4 | 104.8 | 92.1 | 102.8 | 88.2 |

TABLE 11

|  | Comparative Example 5 | | Comparative Example 6 | |
|---|---|---|---|---|
| Hour(hr) | 100 mg | 400 mg | 100 mg | 400 mg |
| 1 | 42.7 | 37.3 | 42.3 | 37.7 |
| 2 | 55.0 | 45.5 | 55.5 | 47.0 |
| 4 | 68.9 | 56.9 | 68.2 | 57.3 |
| 6 | 79.9 | 64.8 | 80.7 | 68.7 |
| 8 | 87.0 | 70.1 | 87.9 | 75.1 |
| 10 | 93.9 | 76.0 | 94.8 | 83.5 |
| 12 | 100.4 | 80.6 | 101.5 | 88.9 |

The dissolution profiles for each preparation are shown in FIGS. 1-17. As shown in FIGS. 1 to 11, which are embodiments of the present invention, the dissolution profiles of lacosamide 100 mg and 400 mg are equivalent to each other. It is generally accepted that the dissolution profiles are equivalent when they have difference within 10%. However, in Comparative Examples 12 to 17, the dissolution profiles were not equivalent to each other depending on the content of lacosamide.

3-5. Beagle Dog PK Evaluation

Pharmaceutical activity of the preparation of Examples was evaluated in the beagle dogs by comparing the dissolution pattern and the pharmacological kinetics of the preparation in order to predict the influence on the efficacy in human body. Experiments were conducted using the tablets prepared according to Example 3 of the paragraph Example 1-1 and commercially available Vimpat tablet 100 mg (Vimpat Tab® Korea UCB Co. Ltd.) as a control preparation. Example 3 was administered orally once a day and the control preparation was administered orally twice a day to beagle dogs about 11 months of age. The control preparation was additionally administered once after blood collection at 12 hours. For the preparation of examples, the blood collection was conducted from the beagle dogs through the jugular vein at 0.5, 1, 1.5, 2, 3, 4, 6, 9, 12, 16, 24, 30 and 36 hours elapse. For the control preparation, the blood collection was conducted from the beagle dogs through the jugular vein at 0.5, 1, 1.5, 2, 3, 4, 6, 9, 12, 12.5, 13, 13.5, 14, 15, 16, 18, 24, 30 and 36 hours elapse. The results are shown in FIG. 18. Blood samples were analyzed by LC-MS to compare PK profiles.

TABLE 12

|  | Cmax(ng/mL) | AUC$_{0 \to 36\ hr}$(ng/mL*hr) | Tmax(hr) |
|---|---|---|---|
| Example 3 | 22681.0 | 143856.6 | 2.5 |
| Control preparation | 19092.4 | 151942.6 | 1.3 |

As a result, as shown in Table 12, the preparation of Example 3 exhibited 94.7% of AUC with respect to the control preparation and 118.8% of Cmax with respect to the control paration. Therefore, it was confirmed that the preparation of Example 3 and the control preparation are biologically equivalent.

The invention claimed is:

1. A pharmaceutical composition comprising lacosamide or a salt thereof as an active ingredient,
    the composition comprising an immediate release layer and an extended release layer,
    wherein the extended release layer comprises cellulose derivative and wax or wax-like lipid in a weight ratio of 1:0.1 to 1:10,
    wherein the pharmaceutical composition is administered orally once a day;
    wherein the pharmaceutical composition is of a two-layered tablet dosage form;
    wherein the cellulose derivative is at least one selected from the group consisting of hydroxypropyl cellulose, hydroxypropyl methylcellulose, ethylcellulose, methylcellulose and hydroxyethyl cellulose;
    wherein the wax or wax-like lipid is at least one selected from the group consisting of glyceryl behenate, glyceryl palmitostearate and glyceryl stearate; and
    wherein the active ingredient in the immediate release layer and the active ingredient in the extended release layer are in a weight ratio of 1:1 to 1:7.

2. The pharmaceutical composition of claim 1, wherein the content of the cellulose derivative and the wax or wax-like lipid is 5 to 50 wt % with respect to the extended release layer.

3. The pharmaceutical composition of claim 1, which is in a dosage form of 100 mg, 200 mg, 300 mg, or 400 mg of lacosamide.

4. A method for treating a subject with epilepsy comprising administering the pharmaceutical composition of claim 1 orally once a day to the subject.

5. The method according to claim 4, wherein the content of the cellulose derivative and the wax or wax-like lipid is 5 to 50 wt % with respect to the extended release layer.

6. The method according to claim 4, wherein the pharmaceutical composition is provided as a dosage form of 100 mg, 200 mg, 300 mg, or 400 mg of lacosamide.

7. The pharmaceutical composition according to claim 1, wherein the immediate release layer further comprises lacosamide or a salt thereof and the extended release layer also comprises lacosamide or a salt thereof.

* * * * *